United States Patent [19]

Kobayashi et al.

[11] Patent Number: 4,848,899
[45] Date of Patent: Jul. 18, 1989

[54] FIXATION SIGHT APPARATUS FOR OPHTHALMOLOGIC INSTRUMENT

[75] Inventors: Katsuhiko Kobayashi; Susumu Takahashi, both of Tokyo, Japan

[73] Assignee: Tokyo Kagaku Kikai Kabushiki Kaisha, Tokyo, Japan

[21] Appl. No.: 874,665

[22] Filed: Jun. 16, 1986

[30] Foreign Application Priority Data

Jun. 18, 1985 [JP] Japan .................................. 60-130898

[51] Int. Cl.$^4$ ................................................. A61B 3/00
[52] U.S. Cl. ..................................... 351/243; 350/602
[58] Field of Search ............... 351/203, 211, 239, 243; 350/109, 602, 447

[56] References Cited

U.S. PATENT DOCUMENTS

| | | | |
|---|---|---|---|
| 1,834,017 | 12/1931 | Carbonara | 350/447 |
| 3,493,290 | 2/1970 | Traub | 350/608 |
| 4,173,398 | 11/1979 | Okamoto et al. | 351/211 |
| 4,679,917 | 7/1987 | Genco et al. | 351/221 |

*Primary Examiner*—Rodney B. Bovernick
*Assistant Examiner*—Jay P. Ryan
*Attorney, Agent, or Firm*—Finnegan, Henderson, Farabow, Garrett & Dunner

[57] ABSTRACT

A fixation sight apparatus for an ophthalmological instrument is disclosed. It has a unique arrangement including light source and mirrors for presenting a plurality of fixation mark images on a measuring optical axis. An eye to be tested selectively fixedly gazes at the most clearly sightable one among the plurality of fixation mark images according to the sight confirmation characteristic thereof.

22 Claims, 5 Drawing Sheets

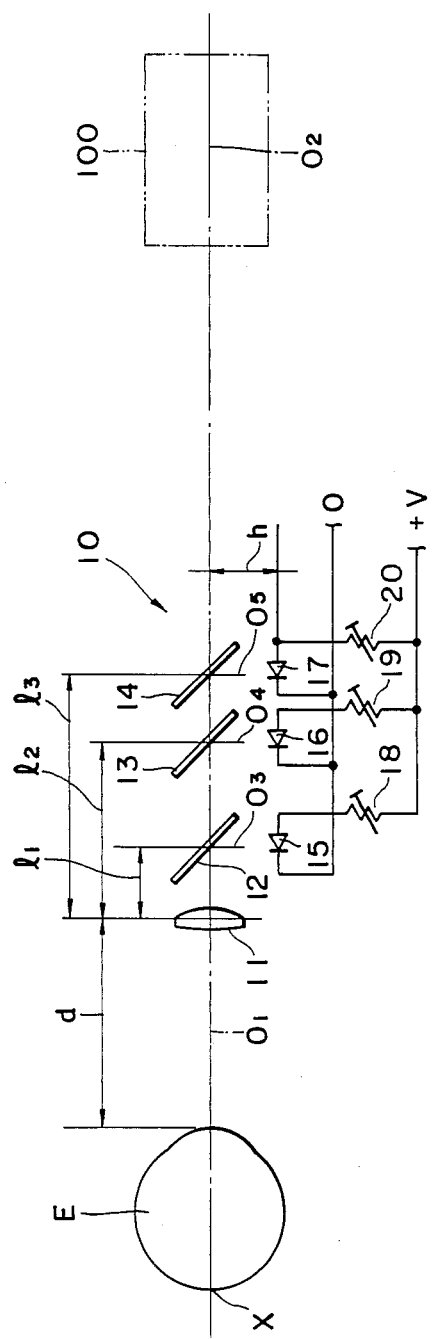
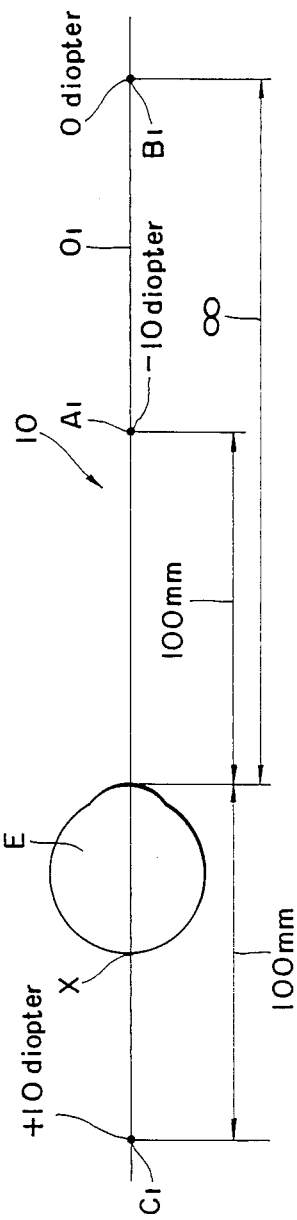

FIXATION SIGHT APPARATUS FOR OPHTHALMOLOGIC INSTRUMENT

BACKGROUND OF THE INVENTION

1. Field of the Invention

This invention relates to a fixation sight apparatus for an ophthalmological instrument to be used for such ophthalmological instruments such as a retinal camera, a refractometer, a tonometer, a perimeter, etc. in order to have an eye to be tested fixedly sight or gaze at a fixation mark.

2. Description of the Related Art

Heretofore, there has been put into actual use an ophthalmological instrument for having a person to be tested fixedly sight or gaze at a fixation mark. In most ophthalmological instruments, a diopter correction mechanism is provided so that even if the eye to be tested is ametropic, myopic, or hyperapic the eye to be tested can fixedly sight the fixation mark.

Two different systems of diopter correction mechanisms are known; one is of the system wherein a plurality of correction lenses having different refractive powers with respect to one another are selectively inserted into an optical path of a fixation sight apparatus, and the other is of the system wherein either one or both of the fixation mark image and the projection lens adapted to project the fixation mark image to the eye to be tested are individually or are simultaneously moved in the optical axis direction thereof to optically position the fixation mark in a far point position of the eye to be tested. Particularly, the latter system is constituted as such that the eye can fixedly sight or gaze at the fixation mark with least accommodation of the eye by optically moving the fixation mark from a position nearer than the far point of the eye to a position farther than the far point position on the optical axis by moving the projection lens.

However, the conventional fixation sight apparatus for ophthalmological instruments including any of the above-mentioned diopter correcting mechanism is complicated in its structure due to the complicated structure of the diopter mechanism employed therein and also the employment of actuation means for actuating the projection lens, correction lens, etc.

Further, although the action of fixedly sighting the eye to be tested on the fixation mark to correct the diopter of the eye is secondary compared to the main measuring and testing actions of the ophthalmological instrument having the fixation sight apparatus, in spite of the foregoing, such a diopter correction operation to actuate the projection lens and the correction lens using the diopter correction mechanism is required to be effected every time the measurement and testing are carried out, which causes the measurer inconveniences.

Moreover, the results corrected by means of the diopter correction operation are required to be confirmed through question and answer between the measurer and the person to be tested. This confirmation action is troublesome. In addition, since the corrected results rely only on the response of the person to be tested, the accuracy thereof is dubious.

SUMMARY OF THE INVENTION

The present invention is accomplished in view of the above situation. It is therefore an object of the present invention to provide a fixation sight apparatus for an ophthalmological instrument, wherein an eye to be tested is enabled to fixedly sight or gaze at a fixation mark without a troublesome operation of diopter correction.

Another object of the present invention is to provide a fixation sight apparatus for an ophthalmological instrument, wherein a fixation mark is presented in such a manner as to adequately decrease the adjusting power of an eye to be tested.

The present invention is accomplished by giving special attention to the sight confirmation characteristic of the human eye wherein when there are presented two images of generaly identically sized-objects overlapping one upon the other, one image being clear and the other being vague, the human brain selects the clear image and brings the attention of the eye to that clear image. It is therefore the feature of a fixation sight apparatus for an ophthalmological instrument according to the present invention that presentation means adapted to present a plurality of fixation mark images is provided on a measuring optical axis.

In the fixation sight apparatus for the ophthalmological instrument according to the present invention, the fixation sight apparatus includes no movable mechanism. Accordingly, the construction is relatively simple when compared with the conventional apparatus. Further, according to the sight confirmation characteristic of the eye to be tested, the most clearly sightable fixation mark image among many fixation mark images can be selected for fixation sight. Accordingly, the question and answer exchanged between the tester and the person to be tested and a correction operation accompanied thereto are not required.

The above and other objects, features and advantages of the present invention will become more apparent to those skilled in the art from the following detailed description of the embodiments of the present invention, when taken in conjunction with the accompanying drawings, wherein:

BRIEF DESCRIPTION OF THE DRAWINGS

FIG. 1 is an illustration of an optical system according to a first embodiment of the present invention;

FIG. 2 is a schematic illustration for explaining the positional relation of an optically conjugate point of a fixation mark image with respect to the retina of an eye to be tested shown in FIG. 1;

DETAILED DESCRIPTION OF THE PREFERRED EMBODIMENTS

The first through seventh embodiments of a fixation sight apparatus for an ophthalmological instrument according to the present invention will be described with reference to the accompanying drawings.

(FIRST EMBODIMENT)

Figure 3:
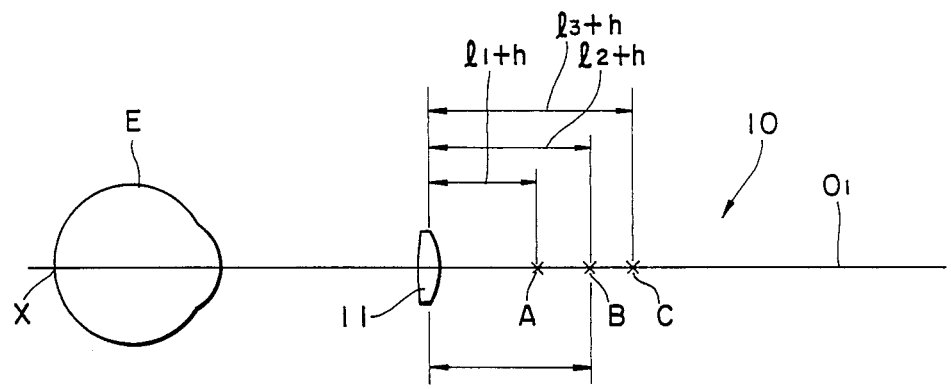
FIG. 3 is an illustration showing the position of a fixation mark image formed by the light emitting diode shown in FIG. 1.

FIGS. 1 through 3 illustrate a first embodiment of a fixation sight apparatus for an ophthalmological instrument according to the present invention. In FIG. 1, reference numeral 10 denotes a fixation optical system of the fixation sight apparatus for an ophthalmological instrument. An optical axis $O_1$ of this fixation optical system 10 and an optical axis $O_2$ of a main optical system 100 of the ophthalmological instrument having this fixation optical system 10 are disposed on one straight line in this embodiment. Reference symbolic character E denotes an eye to be tested which is disposed on the optical axis $O_1$. A projection lens 11 is disposed at a space d in the optical axis direction from the eye. Half mirrors 12, 13 and 14 are disposed respectively behind the projection lens 11 at spaces $l_1$, $l_2$ and $l_3$ along the optical axis $O_1$. These half mirrors 12, 13 and 14 are inclined at angles with respect to the optical axis $O_1$.

On the respective incidence optical axes $O_3$, $O_4$ and $O_5$ of the half mirrors 12, 13 and 14 at a distance h, light emitting diodes 15, 16 and 17 functioning as fixation marks are disposed. The respective anode terminals of the light emitting diodes 15, 16 and 17 are connected with variable resistors 18, 19 and 20 respectively. The brightness of light emitting diodes 15, 16 and 17 are adjusted by adjusting the variable resistors 18, 19 and 20, such that when the light emitting quantity of the light emitting diodes 15, 16 and 17 become adequate with respect to the diopter of the eye E to be tested, the brightness of the entire fixation mark becomes equal to the eye E. In this embodiment, the respective spaces d, $l_1$, $l_2$, $l_3$ and h are set as d=50 mm, $l_1$=6.7 mm, $l_2$=15 mm, $l_3$=20 mm and h=10 mm, and the focal length f of the projection lens 11 is set as f=25.

The light emitting diodes 15, 16 and 17 are simultaneously lit and emitted light of the light emitting diode 15 is reflected by the half mirror 12 and projected toward the eye E by the projection lens 11. In FIG. 3, reference character A denotes a fixation mark based on the light emitting diode 15 formed on the optical axis $O_1$. The fixation mark is formed as a virtual image on the optical axis $O_1$ behind the half mirror 12 by the distance h. The emitted light from the light emitting diode 16 is transmitted through the half mirror 12 after being reflected by the half mirror 13, and is guided to the projection lens 11 and projected toward the eye E by the projection lens 11. In FIG. 3, reference character B denotes a fixation mark based on the light emitting diode 16 formed on the optical axis $O_1$. The fixation mark B is formed as a virtual image behind the half mirror 13 and away therefrom by a space h according to the principle of mirror symmetry. The position of the fixation mark B coincides with the focussing distance f of the projection lens 11. The emitted light from the light emitting diode 17 is transmitted through the half mirrors 13 and 12 in this order after being reflected by the half mirror 14 and is guided to the projection lens 11 and projected to the eye E to be tested by the projection lens 11. In FIG. 3, reference character C denotes a fixation mark based on the light emitting diode 17 formed on the optical axis $O_1$.

Due to the simultaneous lighting of these light emitting diodes 15, 16 and 17, the fixation marks A, B and C are simultaneously presented on the optical axis $O_1$. The light emitting diodes 15, 16 and 17 and the half mirrors 12, 13 and 14 generally constitute a presentation means for presenting the plurality of fixation mark images on the optical axis $O_1$. In this embodiment, since the fixation mark B is located in the focussing position of the projection lens 11, this fixation mark B renders a fixation mark image $B_1$ optically conjugate with the retina X of the eye E to be tested of an emmetropia (0 diopter of refractive power) eye as shown in FIG. 2. Similarly, since the fixation mark A is formed in a position behind the projection lens 11 by a distance of 16.7 mm (equal to 1th), the fixation mark A renders a fixation mark image $A_1$ optically conjugate with respect to the retina X of the eye E of a myopia eye having a refractive power of −10 diopter. Further, since the fixation mark C is formed in a position behind the projection lens 11 by 30 mm (equal to 3+h), the fixation mark C renders a fixation mark image $C_2$ optically conjugated with respect to the retina X of the eye E of a hyperopia eye having a refractive power of +10 diopter.

Due to the foregoing, for example, when the eye E is an emmetropia, a weak myopia, or a weak hyperopia, this eye E can clearly see the fixation mark image $B_1$ by comparing the other two fixation mark images $A_1$ and $C_1$. Accordingly, the eye E fixedly sights or gazes at the fixation mark image $B_1$.

On the other hand, when the eye E to be tested is a strong myopia, the eye E fixedly sights or gazes at the fixation mark image $A_1$ and when the eye E is a strong hyperopia, it fixedly sights or gazes at the fixation mark image $C_1$.

In this embodiment, in order to avoid the differences of the brightness of the fixation mark images $A_1$, $B_1$ and $C_1$, the variable resistors, 18, 19 and 20 are used for adjusting the light emitting quantity of the light emitting diodes 15, 16 and 17. Alternatively, other suitable methods such as a method for varying the duty ratio of the light emitting diodes 15, 16 and 17 and a method for maintaining a difference in reflection or transmission of the respective half mirrors 12, 13 and 14 may be employed.

(SECOND EMBODIMENT)

Figure 4:
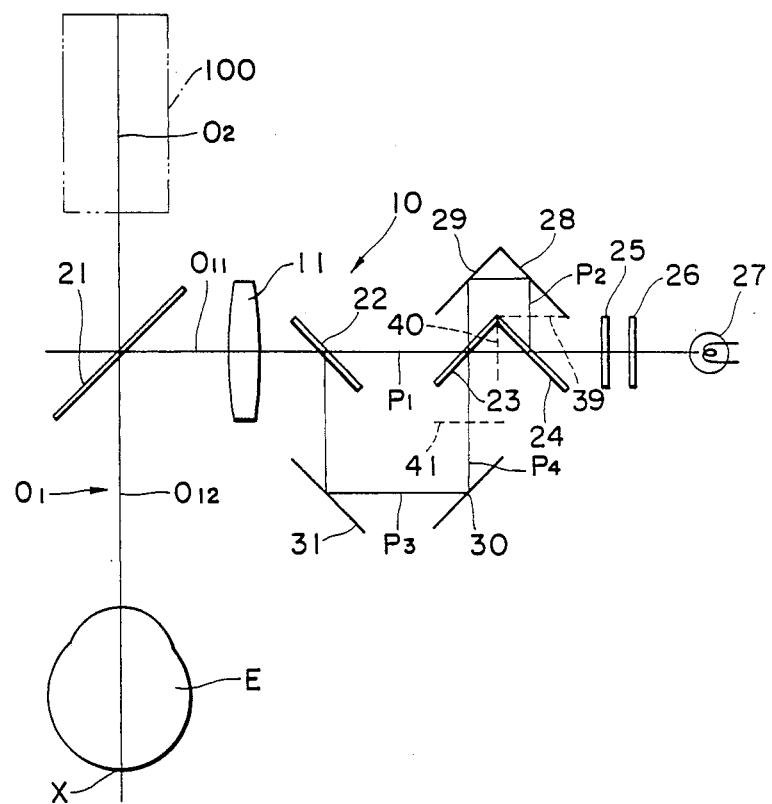
FIG. 4 is an illustration of an optical system for explaining a fixation sight apparatus for an ophthalmological instrument according to a second and a fourth embodiment of the present invention.
Figure 5:
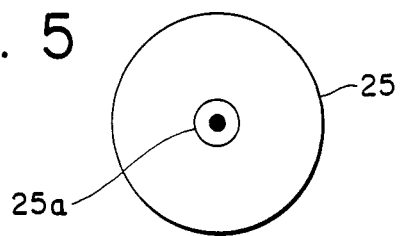
FIG. 5 is a plan view showing one example of a target plate shown in FIG. 4.

FIGS. 4 and 5 illustrate a second embodiment of a fixation sight apparatus for an ophthalmological instrument according to the present invention. The optical axis $O_1$ of the fixation sight apparatus for the ophthalmological instrument is divided into an optical axis $O_{11}$ and an optical axis $O_{12}$ by a half mirror 21, while the optical axis $O_{12}$ and a main optical axis $O_2$ of the main optical system 100 of the ophthalmological instrument are also divided into the respective axes by the half mirror 21. A projection lens 11, half mirrors 22, 23 and 24, a target plate 25, a diffusion plate 26 and an incandescent lamp 27 are disposed on the optical axis $O_{11}$ of the fixation sight apparatus of the ophthalmological instrument. The light emitted from the incandescent lamp 27 illuminates a target plate 25 after being diffused by a diffusion plate 26. The target plate 25 is formed with a ring-shaped fixation mark 25a as shown in FIG. 5.

The light transmitted through fixation mark 25a simultaneously advances along four optical paths as a result of the arrangement of half mirrors 22, 23 and 24. A first optical path $P_1$ is formed in which light is transmitted through the half mirrors 24, 23 and 22 disposed on the optical axis $O_{11}$ and reaches the projection lens 11; a second optical path $P_2$ is formed in which the light is reflected by the half mirror 24, guided to the half mirror 22 through total reflection mirrors 28, 29 and the half mirror 23, is transmitted through the half mirror 22 and reaches the projection lens 11; a third optical path $P_3$ is formed in which the light is reflected by the half mirror 24, is transmitted through the half mirror 23 after being reflected by the total reflection mirrors 28 and 29, guided to the half mirror 22 through total reflection mirrors 30 and 31, and guided to the projection lens 11 by the half mirror 22; and a fourth optical path $P_4$ is formed in which the light is reflected by the half mirror 23, the total reflection mirrors 30 and 31, and the half mirror 22 after being transmitted through the half mirror 24 and guided to the projection lens 11. Due to the foregoing, four fixation mark images are formed on the optical axis $O_1$. And, if the focal length f of the projection lens 11 is set to be equal to the optical path length of, for example, the second optical path $P_2$, the eye E to be tested naturally fixedly sights or gazes at the fixation mark image nearest to the far point of the eye among the simultaneously presented four fixation mark images in the same manner as the first embodiment.

(THIRD EMBODIMENT)

Figure 6:
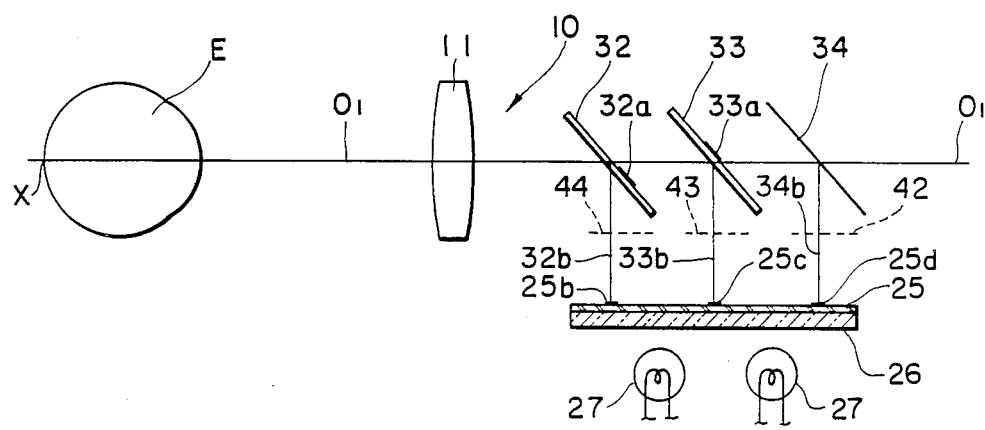
FIG. 6 is an illustration of a circuit for explaining the fixation sight apparatus for an ophthalmological instrument according to the fourth embodiment of the present invention.

FIG. 6 illustrates a third embodiment of a fixation sight apparatus for an ophthalmological instrument according to the present invention, wherein partial mirrors 32 and 33 are used instead of the half mirrors 12, 13 and 14 of the first embodiment. In this apparatus, two incandescent lamps 27 are provided. The light emitted from the incandescent lamps is diffused by a diffusion plate 26. A target plate 25 is formed with three fixation marks 25b, 25c and 25d. The target plate 25 is attached to the diffusion plate 26. The diffusion light illuminates the fixation marks 25b, 25c and 25d. The partial mirrors 32 and 33 are disposed on the optical axis $O_1$ of the fixation sight apparatus of the ophthalmological instrument. A total reflection mirror 34 is disposed behind the partial mirrors 32 and 33. The partial mirrors 32 and 33 partially have reflection films 32a, 33a on a transparent glass and are inclined at angles with respect to the optical axis.

The reflection film 32a of the partial mirror 32 and the reflection film 33a of the partial mirror 33 are formed within an area where they do not optically interfere with respect to each other and within a very small area close to the optical axis $O_1$ disposed therebetween. On the incidence optical axes 32b, 33b and 34b of the respective mirrors 32, 33 and 34, the respective fixation marks 25b, 25c and 25d are located. The focal point of the projection lens 11 is in an optically conjugate position with the fixation mark 25c of the incidence optical axis 33b in the same manner as the first embodiment.

Due to the foregoing construction, the projection lens 11 projects a fixation light formed by three fixation marks 25b, 25c and 25d toward the eye E to be tested to form three fixation mark images $A_1$, $B_1$ and $C_1$ on the optical axis $O_1$ in the same manner as the first embodiment. The eye to be tested naturally fixedly gazes at the fixation mark image nearest to the far point which the eye E itself has.

(FOURTH EMBODIMENT)

In the first through the third embodiments, a plurality of fixation mark images are simultaneously presented on the optical axis $O_1$ of the fixation sight apparatus for the ophthalmological instrument in order to have the eye E to be tested confirm them by sight. However, the present invention is not limited to the foregong. There will be described another embodiment hereinafter in which additional structure is employed in addition to the construction of the first through the third embodiments in order to selectively present the fixation mark images to the eye E to be tested. Further, there will be described a foggy sight like sight fixation means in which the order of the presentation of the fixation marks is predetermined to remove the accommodation of the eye E and have the eye E fixedly sight or gaze at the proper fixation mark.

Figure 7:
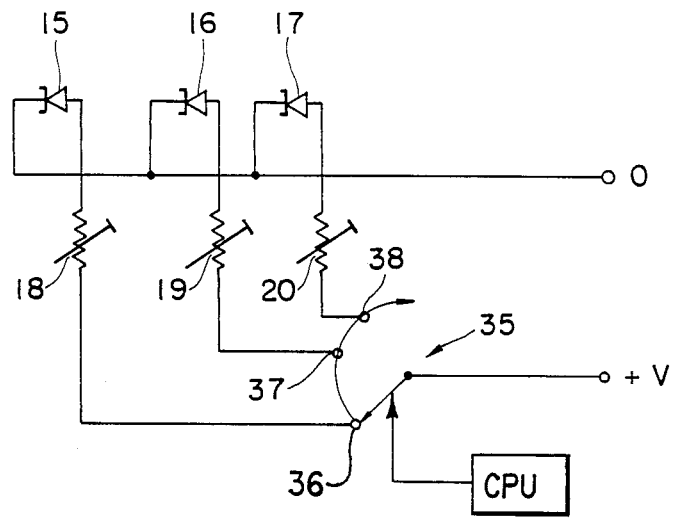
FIG. 7 is an illustration of an optical system for explaining a fixation sight apparatus for an ophthalmological instrument according to a third embodiment of the present invention.

(1) FIG. 7 illustrates a modified embodiment of the first embodiment and is a circuit for showing the construction for selectively presenting the fixation mark images to the eye E to be tested. In FIG. 7, identical elements as those of the first embodiment are denoted by the identical numerals or characters as those used in the first embodiment, and the detailed description on them will be omitted. Instead, only the different structure will be described.

In this modified embodiment, between a (+) anode terminal of an electric power source and light emitting diodes 15, 16 and 17, a switch 35 is interposed. The switch 35 has three terminals 36, 37 and 38. The terminal 36 is connected with an anode of the light emitting diode 15 through a variable resistor 18, the terminal 37 is connected with an anode of the light emitting diode 16 through a variable resistor 19 and the terminal 38 is connected with an anode of the light emitting diode 17 through a variable resister 20.

With this construction, the light emitting diodes 15, 16 and 17 can be selectively lighted by activating the switch 35 in order. Accordingly, the fixation mark images can be selectively presented to the eye E to be tested. Particularly, if the switch 35 is turned in the clockwise direction as shown in FIG. 7, the fixation mark images $A_1$, $B_1$ and $C_1$ are presented in order starting from the far point position of myopia to the far point position of emmetropia, and to the far point position of hyperopia. Accordingly, the eye E to be tested fixedly sighting or gazing at the image is decreased in its accommodation, thereby enabling the eye to fixedly sight or gaze in a state near to non-accommodation. Thus, a foggy sight like fixation sight is obtainable.

The switching operation of the switch 35 may be effected manually or automatically. For example, it can be automatically operated by connecting it to a CPU circuit operably associated with the ophthalmological instrument.

DESCRIPTION OF THE MODIFICATIONS OF THE SECOND AND THE THIRD EMBODIMENTS

The modified embodiments are constructed such that as shown in FIGS. 4 and 6, liquid crystal shutters 39 through 45 are arranged within the respective optical paths and the fixation mark images are selectively presented to the eye E to be tested by putting on or off the liquid crystals shutters 39 through 45. One such example will be described with reference to the modified embodiment shown in FIG. 4. If the shutters 39, 41 are put on and the shutter 40 is put off, only the first optical path $P_1$ is selected. If the shutters 40, 41 are put on and the shutter 39 is put off, only the second optical path $P_2$ is selected. Likewise, if the on-off operation of these shutters 39, 40 and 41 are effected at predetermined intervals in turn, the fixation mark images $A_1$, $B_1$ and $C_1$ are presented starting from the far point of myopia to the far point of hyperopia, thereby enabling the eye E to be tested with a foggy sight like fixation sight.

(FIFTH EMBODIMENT)

Figure 8:
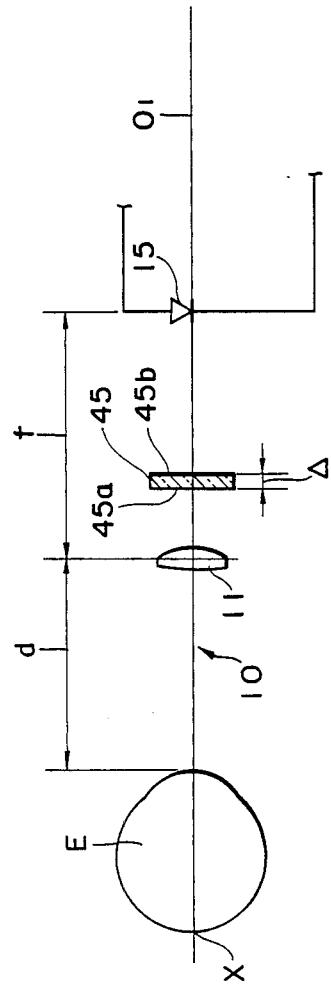
FIG. 8 is an illustration of an optical system for explaining a fixation sight apparatus for an ophthalmological instrument according to a fifth embodiment of the present invention.
Figure 9:
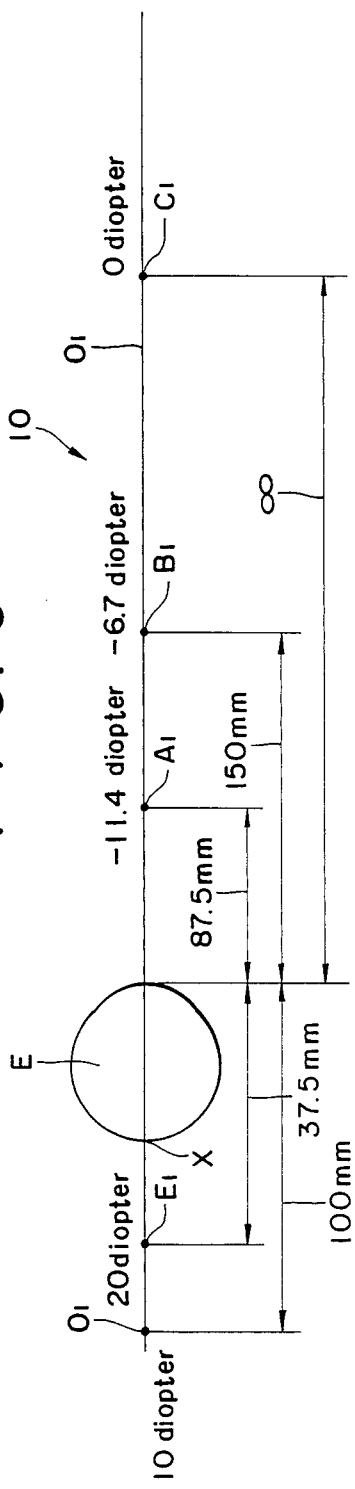
FIG. 9 is a schematic illustration for explaining the relation in the optically conjugate point between the retina of the eye to be tested and the fixation mark image shown in FIG. 8.
Figure 10:
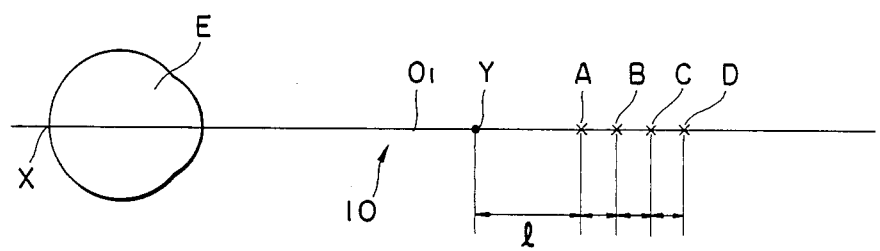
FIG. 10 is an illustration of an optical system showing a fixation sight apparatus for an ophthalmological instrument according to a sixth embodiment of the present invention.

FIGS. 8 through 10 illustrate a fifth embodiment of a fixation sight apparatus for an ophthalmological instrument according to the present invention. In this embodiment, between a light emitting diode 15 serving as a fixation mark and a projection lens 11, a plane parallel glass plate 45 is disposed in such a manner as to be perpendicular to the optical axis $O_1$. Both surfaces of the plane parallel plate 45 serve as half mirror surfaces 45a and 45b. Further, in this embodiment, the distance d between the eye E to be tested (fixedly sighting eye) and the projection lens 11 is set as d=25 mm, the focal length f of the projection lens 11 is set as f=15 mm, and the light emitting diode 15 is disposed at the focal point of the projection lens 11. The optical thickness of the plane parallel plate 45 can be obtained as $\Delta/n$, if the geometrical thickness is put as $\Delta$, and the refractive index of the glass is put as n. In this embodiment, it is set as $\Delta/n=2.5$ mm.

In this embodiment, a part of the light emitted from the light emitting diode 15 is allowed to transmit through the plane parallel plate 45. However, the remaining emitted light transmits the plane parallel plate 45 and is guided to the projection lens 11 after being reflected a plurality of times on the half mirror surfaces 45a and 45b. Accordingly, an infinite number of fixation marks A, B, C, D . . . are formed on the optical axis $O_1$ as shown in FIG. 10. In FIG. 10, reference character Y denotes an optical position of the projection lens 11.

The relation between the retina X of the eye E to be tested and the fixation mark images $A_1$, $B_1$, $C_1$, $D_1$, $E_1$ . . . positioned in optically conjugate position with respect to the retina X is shown in FIG. 9. The eye E fixedly sights or gazes at one fixation mark image positioned nearest to the optically conjugate position on its own retina X, at the time when no accommodation is effected, among these fixation mark images.

A light quantity attenuation takes place due to the plural times reflection and transmission occurs through the half mirror surfaces 45a and 45b and the brightness of the fixation marks A, B, C, D . . . is decreased in turn. Accordingly, in order to prevent the occurrence of the light quantity attenuation, the reflectance of the half mirror surfaces 45a and 45b is set as 95% and the transmittance is set as 5% in this embodiment.

(SIXTH EMBODIMENT)

Figure 11:
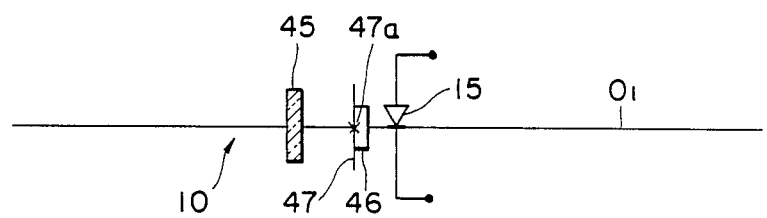
FIG. 11 is an illustration of an optical system showing a fixation sight apparatus for an ophthalmological instrument according to a seventh embodiment of the present invention.

FIG. 11 illustrates an embodiment showing a first modified embodiment of the fifth embodiment, wherein a diffusion plate 46 is disposed between the light emitting diode 15 and the plane parallel plate 45. A pin hole plate 47 is placed in contact with the diffusion plate 46. The pin hole plate 47 is formed with a pin hole 47a. In this embodiment, the size of the pin hole represents the size of the fixation mark. If the construction of this embodiment is combined with the afore-mentioned construction in which the light emitting diode 15 itself is directly used as a fixation mark, freedom for selecting the size of the fixation mark is increased.

(SEVENTH EMBODIMENT)

Figure 12:
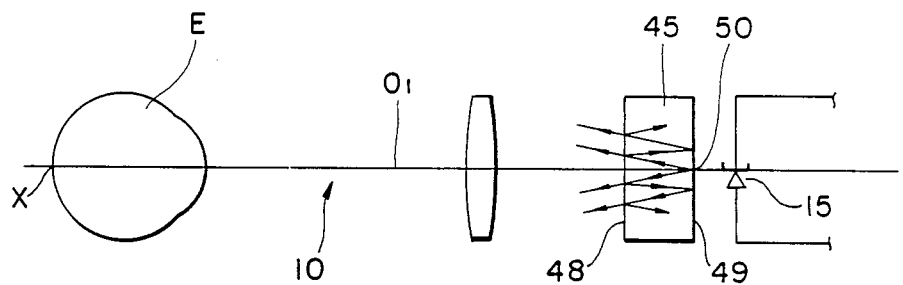
FIG. 12 is an illustration of an optical system showing the fixation sight apparatus for an ophthalmological instrument according to the sixth embodiment of the present invention.

FIG. 12 illustrates an embodiment showing a second modified embodiment of the fifth embodiment, wherein only a front surface 48 of the plane parallel 45 serves as a half mirror surface, and a rear surface 49 serves as a total reflection surface having a pin hole 50 on the optical axis $O_1$. By utilizing the phenomenon that the light emitting diode 15 transmits light through the pin hole 50 and that light is diffused by passing through pin hole 50, the light is repeatedly reflected and transmitted plural times between the half mirror surface 48 and the total reflection surface 49 to form a plurality of fixation mark images A, B, C, D . . . on the optical axis $O_1$.

Although the present invention has been described with reference to the preferred embodiments, many modifications and alterations may be made within the spirit of the present invention.

What is claimed is:

1. A fixation sight apparatus for an ophthalmological instrument comprising:
   optical projection means, having a fixation optical axis and a focal length thereof, for projecting a plurality of fixation marks;
   fixation mark formation means for forming, simultaneously, from said plurality of fixation marks, at least first, second and third fixation marks on said fixation optical axis;
   said first fixation mark being formed at a position behind said optical projection means by a distance shorter than said focal length;
   said second fixation ark being formed at a position behind said optical projection means by a distance which is equal to said focal length; and
   said third fixation mark being formed at a position behind said optical projection means by a distance which is longer than said focal length;
   images of said first, second, and third fixation marks which ae simultaneously projected by said optical projection means toward an eye to be tested being optically conjugate, respectively, to far points of a myopic eye to be tested having some negative refractive power, an emmetropic eye to be tested having zero refractive power, and a hyperopic eye to be tested having some positive refractive power; and
   whereby the most clearly viewable fixation mark image among said fixation mark images can be selected for fixation sight in accordance with the sight confirmation characteristic of the eye to be tested.

2. A fixation sight apparatus according to claim 1, wherein said fixation mark formation means comprises:
a light source disposed on said fixation optical axis;
a plane parallel glass plate disposed perpendicularly on said fixation optical axis and which is formed at both sides thereof with half mirror surfaces;
said light source functioning as said second fixation mark, and said plane parallel glass plate functioning to simultaneously form said first and said third fixation marks.

3. A fixation sight apparatus according to claim 1, wherein said fixation mark formation means comprises:
a light source disposed on said fixation optical axis;
a plane parallel glass plate disposed perpendicularly on said fixation optical axis and which includes a first side, disposed proximate said light source, having a total reflection surface formed thereon, and a second side, opposing said first side, having a half mirror surface formed thereon;
a pin hole formed in said total reflection surface and disposed on said fixation optical axis;
said pin hole functioning as said second fixation mark, and said plane parallel glass plate functioning to simultaneously form said first and said third fixation marks.

4. A fixation sight apparatus according to claim 1, wherein said fixation mark formation means comprises:
a light source;
a pin hole plate having a pin hole disposed on said fixation optical axis;
a plane parallel glass plate disposed perpendicularly on said fixation optical axis and which includes first and second opposing sides thereof, each said side having a half mirror surface formed thereon;
said pin hole functioning as said second fixation mark, and said plane parallel glass plate functioning to simultaneously form said first and said third fixation marks.

5. A fixation sight apparatus for an ophthalmological instrument according to claim 4, utilized in combination with at least one of a retina camera, a refractometer, a tonometer, a perimeter and a corneal configuration measuring apparatus.

6. A fixation sight apparatus according to claim 1, wherein said fixation mark formation means comprises:
at least three half mirrors each disposed obliquely and spaced from one another on said fixation optical axis;
at least three light sources each disposed on respective incident optical axes of said half mirrors; and
said light sources corresponding to said first, said second and said third fixation marks, respectively.

7. A fixation sight apparatus according to claim 6, further including means for independently and selectively adjusting the light emitting quantities of said light sources.

8. A fixation sight apparatus according to claim 1, wherein said fixation mark formation means comprises:
at least one light source;
a target plate having at least three target marks formed thereon and illuminated by said light source;
at least three half mirrors disposed obliquely on said fixation optical axis and spaced from one another, each said half mirror having an incident optical axis coincident with respective ones of said target marks; and
said target marks corresponding to said first, said second and said third fixation marks, respectively.

9. A fixation sight apparatus according to claim 1, wherein said fixation mark formation means comprises:
a light source;
a target plate having a target mark disposed on said fixation optical axis and illuminated by said light source;
an optical system including a plurality of half mirrors arranged obliquely on said fixation optical axis, and a plurality of total reflection mirrors disposed off said fixation optical axis and in parallel with said half mirrors; and
said half mirrors and said total reflection mirrors forming at least three optical paths of light from said target mark, each said optical path having a different optical path length relative one another, and at least a portion of each said optical path being coincident with the others of said optical paths and with said fixation optical axis.

10. A fixation sight apparatus for an ophthalmological instrument comprising:
optical projection means, having a fixation optical axis and a focal length thereof, for projecting a plurality of fixation marks;
fixatiion mark formation means for forming, selectively, from said plurality of fixation marks, at least first, second and third fixation marks on said fixation optical axis;
said first fixation mark being formed at a position behind said optical projection means by a distance which is equal to said focal length;
said second fixation mark being formed at a position behind said optical projection means by a distance which is shorter than said focal length;
said third fixation mark being formed at a position behind said optical projection means by a distance which is longer than said focal length;
images of said first, second, and third fixation marks which are simultaneously projected by said optical projection means toward an eye to be tested being optically conjugate, respectively, to far points of a myopic eye to be tested having some negative refractive power, an emmetropic eye to be tested having zero refractive power, and a hyperopic eye to be tested having some positive refractive power; and
whereby the most clearly viewable fixation mark image among said fixation mark images can be selected for fixation sight in accordance with the sight confirmation characteristic of the eye to be tested.

11. A fixation sight apparatus according to claim 10, wherein said fixation mark formation means comprises:
at least three half mirrors each disposed obliquely and spaced from one another on said fixation optical axis;
at least three light sources each disposed on respective incident optical axes of said half mirrors;
said light sources corresponding to said first, said second and said third fixation marks, respectively; and
selection means for selecting at least one of said first, said second and said third fixation marks formed on said fixation optical axis to be projected toward the eye to be tested.

12. A fixation sight apparatus according to claim 11, wherein said selection means includes switch means for selectively activating at least one of said light sources and selectively deactivating the remaining ones of said light sources.

13. A fixation sight apparatus according to claim 12, wherein said switch means includes control means for automatically and selectively activating and deactivating said light source.

14. A fixation sight apparatus according to claim 11, wherein said selection means includes at least three shutters, each of said shutters being selectively operable to an open and a closed position and disposed on respective ones of said incident optical axes of said half mirrors, and means for opening and closing selected combinations of said shutters to selectively project at least one of said fixation mark images toward the eye to be tested.

15. A fixation sight apparatus according to claim 14, wherein each of said shutters includes a liquid crystal.

16. A fixation sight apparatus according to claim 11, further including means for selectively and independently varying the quantity of light emitted from said light source.

17. A fixation sight apparatus according to claim 10, wherein said fixation mark formation means comprises:
   at least one light source;
   a target plate having at least three target marks which correspond to respective ones of said fixation marks and which are illuminated by said light source;
   at least three half mirrors spaced from one another and fixedly and obliquely disposed on said fixation optical axis, each incident optical axis of said half mirrors being coincident with a respective one of said target marks; and
   said selection means including at least three shutters, each said shutter being disposed on said respective incident optical axis of each said half mirror and alternately operable to an open and a closed position, and means for activating a selected combination of said shutters to one of said open and closed positions, respectively.

18. A fixation sight apparatus according to claim 17, wherein each of said shutters includes a liquid crystal.

19. A fixation sight apparatus according to claim 10, wherein said fixation mark formation means comprises:
   at least one light source;
   a plurality of partial mirrors spaced from one another and disposed fixedly and obliquely on said fixation optical axis such that interference between light reflected by respective ones of said partial mirrors is substantially eliminated;
   a target plate having a plurality of target marks which correspond to respective ones of said fixation marks and each of which is coincident with respective ones of incident optical axes of said partial mirrors, and each of which are illuminated by said light source;
   selection means including a plurality of shutters, each said shutter being disposed on respective ones of said incident optical axes, and each said shutter having an open and a closed position; and
   means for activating said shutters to a selected combination of said open and closed positions, respectively.

20. A fixation sight apparatus according to claim 19, wherein each of said shutters includes a liquid crystal.

21. A fixation sight apparatus according to claim 10, wherein said fixation mark formation means comprises:
   a light source;
   a target plate having a target mark disposed on said fixation optical axis and illuminated by said light source;
   an optical system including a plurality of half mirrors spaced from one another and fixedly and obliquely disposed on said fixation optical axis, and a plurality of total reflection mirrors which are fixedly disposed off said fixation optical axis and which are obliquely arranged in parallel with respective ones of said half mirrors, said half mirrors and said total reflection mirrors being operably positioned to form a plurality of optical paths each having a different optical path length relative one another, at least a portion of each said optical path being coincident with said fixation optical axis; and
   a plurality of shutters, respective ones of said shutters being disposed on respective ones of said optical paths of said optical system, each said shutter being alternately operable to an open and a closed position, and means for activating said shutters to a selected combination of open and closed positions to selectively form one of said fixation marks on said fixation optical axis.

22. A fixation sight apparatus according to claim 21, wherein each of said shutters includes a liquid crystal.

* * * * *